United States Patent [19]

St. Martin

[11] Patent Number: 4,927,760

[45] Date of Patent: May 22, 1990

[54] PRODUCTION OF CRYSTALLINE PIGMENTS FROM MONASCUS DURING FERMENTATION

[75] Inventor: Edward J. St. Martin, Libertyville, Ill.

[73] Assignee: UOP, Des Plaines, Ill.

[21] Appl. No.: 366,726

[22] Filed: Jun. 15, 1989

Related U.S. Application Data

[63] Continuation-in-part of Ser. No. 261,811, Oct. 24, 1988, abandoned.

[51] Int. Cl.$^5$ .......................... C12P 1/02; C12P 7/48; C12N 9/02; C12N 9/06
[52] U.S. Cl. .................... 435/171; 435/144; 435/191; 435/911; 435/189
[58] Field of Search ............... 435/144, 171, 191, 911, 435/189

[56] References Cited

U.S. PATENT DOCUMENTS 4,145,254  3/1979  Shepherd et al. .................. 195/81
4,442,209  4/1984  Miyake et al. .................... 435/119

OTHER PUBLICATIONS

*Food Technology*, p. 49 (Jul., 1986).
B. C. Fielding et al., *Tetrahedron Letters*, No. 5, 24–7 (1960).
Kumasaki et al., *Tetrahedron*, 18, 1171 (1962).
Lin, *J. Ferment. Technol.*, 51, 407 (1973).
Hawksworth and Pitt, *Aust. J. Bot.*, 31, 51 (1983).

*Primary Examiner*—Ronald W. Griffin
*Assistant Examiner*—Pamela S. Webber
*Attorney, Agent, or Firm*—Thomas K. McBride; Eugene I. Snyder

[57] ABSTRACT

Both the ease and cost of isolating the water insoluble orange pigment produced as a secondary metabolite by Monascus species can be substantially improved by inducing crystalline pigment formation directly in the culture medium. Poly(oxyethylene)sorbitan esters of palmitic acid are especially effective and cause the formation of large crystals. Another class of crystalline pigment inducing agents is that of the liquid vegetable oils, although generally these lead to smaller crystal sizes.

6 Claims, No Drawings

PRODUCTION OF CRYSTALLINE PIGMENTS FROM MONASCUS DURING FERMENTATION

CROSS REFERENCE TO RELATED APPLICATION

This application is a continuation-in-part of my co-pending application, Ser. No. 261,811, filed Oct. 24, 1988, now abandoned, all of which is hereby incorporated by reference.

BACKGROUND OF THE INVENTION

"We live in a world of color- color is in the trees and sky around us, in our clothes, and in our homes. When the colors of familiar things differ from what we expect, we are usually upset - greenish skies warrant of bad weather, black clothes denote mourning, intense colors in the home stimulate or agitate. The same applies to food. Consumers first judge the quality of the food product by its color." Food Technology, page 49 (July, 1986). However much one may decry a consumer attitude which places higher priority on visual impact than on gustatory and nutritional value, it is an attitude which must be actively confronted in the marketplace.

Although naturally occurring pigments perforce were the first used food colorants, the development of chemistry as a discipline led to many synthetic dyes, especially anilines, to supplant naturally occurring pigments as food additives. As a class synthetic colorants have many advantages, such as a uniform and reproducible color, color stability, absence of flavor, and an oxidative and/or thermal and/or light stability superior to naturally occurring pigments, broad availability relatively insensitive to changes in crop yields, and so forth. As a result, the popularity of synthetic colorants at least is understandable.

However, with heightened awareness of a consuming public to food additives and increased testing of some representative examples came a concern about their safety. Recent years have seen some materials formerly used as food colorants run the gamut from being beyond reproach to being suspect and even banned or at least used restrictedly. For example, FD&C Red No. 2 and FD&C Violet No. 1 have been banned in the United States and many other countries. Because of a variety of allergic reactions in sensitive individuals induced by FD&C Yellow No. 5 a recent ruling by the FDA requires food colored with it be declared as such on product labels. As a consequence the pendulum has begun to swing once more toward naturally occurring pigments as food additives.

The pigments produced by Monascus species fungi traditionally grown on rice in the Orient are orange and relatively insoluble in water, but readily react with compounds containing amino groups to form water soluble colorants. Monascus pigments have been used in the Orient for hundreds of years as a general food colorant and as a colorant for wine and bean curd. The pigments can be made water soluble or oil soluble, are stable at a pH range 2-10, are heat stable and can be autoclaved. In oriental countries microorganisms of this type typically are grown on grains of rice and once the grains have been penetrated by the red mycelium the whole mass is finely ground with the resulting powder used as a food colorant. The orange pigment is a mixture of monascorubrin and rubropunctatin, whose structures were elucidated by B. C. Fielding et al., Tetrahedron Letters No. 5, 24–7 (1960) and Kumasaki et al., Tetrahedron, 18, 1171 (1962), which differ in the former having a 7-carbon ketonic group and the latter having a 5-carbon ketonic group. For the purposes of this application, "Precursor pigment" refers to any mixture of water insoluble orange pigment containing monoascorubrin and rubropunctatin as produced by fermentation of a suitable Monascus species.

Commercial production of precursor pigment requires development of a suitable fermentation procedure, which has been the subject of many reports in recent years. Shepherd et al., U.S. Pat. No. 4,145,254, made an important advance by using a process with two phases in which the microorganism first was cultivated at pH 4–7 in a growth-promoting medium, then was transferred to a second medium at pH 2–4 to stimulate precursor pigment production. The low pH did not interfere with precursor pigment production but inhibited its subsequent reaction with amino groups of proteins and/or ammonium ions in the medium. The result was the exclusive production of orange precursor pigment as a colorant. As another example U.S. Pat. No. 4,442,209 claims to increase precursor pigment formation by cultivating a Monascus species in a medium containing maltitol.

As Shepherd et al. noted, ". . . if it is desired commercially to obtain a pigment having a perfectly determined structure which may be subjected to rigorous tolerance tests and which shows perfectly reproducible properties, it is the high-yield production of a high-purity orange pigment which should be researched in the first instance." All processes described to date retain serious disadvantages associated with the separation and isolation of high purity precursor pigment. More particularly, in the prior art processes precursor pigment is formed as an amorphous, clumpy mass, which is believed to be a consequence of some type of pigment-lipid association. This solid mass is not separable from the mycelium, as by partitioning into another phase; the strong association of the precursor pigment with fungal-produced lipids makes pigment extraction and purification very difficult, onrous, and costly. A perhaps typical prior art method utilizes the extraction of the pigment production medium with an organic solvent after separation of mycelium, or extraction of the production medium containing homogenized mycelium with an organic solvent. The solvent then is evaporated to afford crude precursor pigment which is subsequently further purified, as by chromatography and crystallization for example. Such an extraction-chromatography-crystallization procedure is inefficient as regards yield of the purified precursor pigment, costly because of the use of solvents to extract the pigment and the necessity of expanding energy to evaporate solvent from the extract, and not readily adaptable to continuous fermentation with continuous precursor pigment production.

Although there may be other aspects of precursor pigment production from Monascus which need attention, for example, obtaining suitable mutants or otherwise genetically altered microorganisms, this application is directed solely to an improvement in precursor pigment production which eliminates the need for costly extraction methods. Specifically, I have discovered that if during fermentation of pigment-producing Monascus species the medium contains certain added materials, precursor pigment is formed in a crystalline state, relatively pure per se and unassociated with fungal-produced lipids. Equally important is the observation that the precursor pigment crystals so formed can be readily partitioned into an oil phase, affording their facile separation from the mycelium and fermentation medium. The theoretical basis of the invention herein is uncertain, but it may be that certain materials act as biochemical regulators which block lipid synthesis while not affecting precursor pigment production. Whatever the theoretical basis, the effect of the addition of these biochemical modulators is that precursor pigment is excreted from the cell and rapidly forms large bright orange crystals which can be collected. The crystals are rather pure and ordinarily need not be further purified prior to their use. The process based on this discovery produces precursor pigments from glucose as a carbon source with 7% efficiency and is readily adapted to continuous fermentation. As will be readily recognized, the process also is independent of the particular microorganism producing the precursor pigment and the medium in which the microorganism is grown.

SUMMARY OF THE INVENTION

The purpose of this invention is to increase the ease and efficiency of isolation on the water insoluble orange pigment produced by Monascus species under fermentation conditions. An embodiment comprises culturing Monascus species in a pigment producing culture medium containing a crystalline pigment inducer in an amount effective to induce crystalline pigment formation. In a particular embodiment the inducer is a liquid vegetable oil. In another specific embodiment the crystal inducer is a poly(oxyethylene)sorbitan ester of palmitic acid. In a still more specific embodiment the inducer is a poly(oxyethylene)-sorbitan ester of palmitic acid present in the pigment producing culture medium at a level of between about 0.1 and about 1 weight percent. Other embodiments will be apparent from the following description.

DESCRIPTION OF THE INVENTION

The observation that forms the basis of this invention is that when Monascus species are grown in a pigment producing culture medium, pigment can be induced to form as crystals when the medium contains certain additives. The crystalline pigment formed is not associated with the mycelium, which stands in contrast to the situation in the absence of the crystal inducers of this invention, and as a consequence the pigment can be isolated rather simply by collection of the crystals rather than by extraction of a homogenized fermentation broth. As a consequence the process based on this observation allows a more efficient pigment isolation at an appreciably lower cost than that previously possible. Additionally, the process does not kill Monascus fungal cells during pigment isolation, thereby providing an opportunity for cell recycling and a continuous pigment production process.

It bears emphasis that the thrust of my invention is the formation of crystalline precursor pigment directly from the fermentation broth where it is produced. The additives of my invention do not induce pigment production, but rather induce crystallization of the pigment as produced during fermentation. The success of my invention is therefore independent of, and unconnected with, the particular Monascus species used so long as the latter produces sufficient pigment to exceed its solubility limits in the fermentation medium. Particular Monascus species may have important effects on, e.g., the level and the rate of precursor pigment production, but nonetheless have no influence upon effecting crystalline precursor pigment formation.

As previously stated, Monascus species have long been known to make as a metabolite a water insoluble orange pigment as a mixture of monascorubrin and rubropunctatin, which we refer to in this application as precursor pigment. There may be used in the practice of my invention any Monascus species which produces precursor pigment in an amount sufficient to exceed its solubility limits in the pigment producing culture medium. For all practical purposes, this requirement translates to formation of at least 30 milligrams per liter of precursor pigment at pigment producing conditions. Suitable Monascus species are readily obtainable from various sources. For example, Lin [J. Ferment. Technol., 51, 407 (1973)] has described numerous isolates from Koji (sediment) of Koaliang brandy. Similar isolates can be easily obtained from other oriental fermented foods colored with the Monascus mold, such as red rice, red rice wine and red soybean cheese. Lin also has reported numerous species publicly available as type cultures from several sources. In their taxonomic study Hawksworth and Pitt [Aust. J. Bot., 31, 51 (1983)] examined a multitude of isolates, many of which were publicly available from depositories or readily isolated from oriental fermented food.

From the foregoing it needs to be noted that suitable strains of Monascus species occur widely, that many are available from depositories, and that still more can be routinely isolated from oriental fermented food. Thus, subject to the requirement of a rather modest level of precursor pigment production the Monascus strains used in the practice of our invention are merely a matter of choice with a very large number of strains readily available to anyone. Although such species as *M. purpureus, M. major, M. rubiginosus* and *M. Anka* have been cited as precursor pigment producers, the taxonomic work of Hawksworth and Pitt suggests these may need to be reclassified.

As Shepherd et al. have pointed out in U.S. Pat. No. 4,145,254 it is possible to grow Monascus species under conditions which are capable of completely inhibiting the production of secondary metabolites such as the precursor pigment. For the purpose of this invention it is necessary that Monascus be grown in a pigment producing culture medium. In this invention the pigment producing culture medium needs to be at a pH between about 2 and about 4 during the pigment producing phase. A generalized pigment production culture medium may contain $KH_2PO_4$ (1–100 mM), $MgSO_4$ (0.1–10 mM), NaCl (110 mM), $FeSO_4$ (0.01–1.0 mM) and $NH_4Cl$ or $KNO_3$ (1–20 mM). Several carbohydrates can be used as a source of carbon and energy for pigment production at a concentration of 0.1 to 40% and can include complex carbohydrates such as starch, disaccharides such as sucrose or lactose and monosaccharides such as glucose or fructose, with the preferred substrate being glucose.

The growth of Monascus species in suitable media to produce precursor pigment is well known, and what distinguishes our invention over the prior art is that the precursor pigment producing culture medium contains additives (crystalline pigment inducing agents or inducers) which induce crystallization of the pigment as formed. Such inducers are of various types, one of which is the class of poly(oxyethylene)sorbitan esters, whose members commonly are known under the trademark of TWEEN. In particular, TWEEN 20, TWEEN 40, and TWEEN 80 have been found to be particularly effective not only in inducing crystalline pigment formation, but also in producing large crystals, i.e., crystals at least 10 microns long. All the aforementioned TWEENS are a mixture of esters whose fatty acid component includes palmitic acid. The TWEENS may be effective at a concentration as low as about 0.01 weight percent, but it is recommended that they be used at a concentration of at least about 0.1 and as high as about 1 weight percent in the culture medium. Higher percentages of TWEEN may be used, although not with any apparent incremental benefits. When using TWEEN as a crystal inducer, as with the other crystal inducers of this invention, it is necessary that there be good mixing of the culture medium to ensure adequate dispersion of the crystal inducer.

Another class of crystal inducers consists of liquid vegetable oils, especially corn oil and soybean oil, but including such materials as cottonseed, palm, peanut, sunflower, safflower, sesame, rapeseed and olive oils. Although the vegetable oils are effective when added in an amount between about 0.1 and about 10 weight percent of the culture medium, the crystals so produced often are relatively small, i.e., less than 10 microns long. Since the oils are not soluble in the fermentation medium their use results in emulsions which can hinder good aeration of the fungus during pigment production. Additionally, the oils may hydrolyze in part during fermentation to free fatty acids which form insoluble films in the oil. Finally, the pigment is somewhat soluble in liquid vegetable oils and a portion, which may be large, of the pigment may be lost during harvesting of the crystals. These features make the use of liquid vegetable oils less desirable than the use of TWEEN as a crystalline pigment inducing agent.

A third class of crystalline pigment inducers consists of glycerol triesters. Triacetin, triarachidin, tributyrin, trilinolenin, tripalmitin and tristearin led to small crystals of marginal benefit. However, triolein, tripalmitolein and tripetroselinin led to good production of large crystals, and these materials, or any combination of them, are especially recommended in the practice of this invention. It also can be anticipated that triglycerides whose fatty acid residues are palmitic, palmitoleic, oleic, or petroselinic acid in any combination may be effective crystalline pigment inducers.

In the production of crystalline precursor pigment, a Monascus species typically is grown in a pigment producing culture medium containing an amount of a crystalline pigment inducer effective to induce crystalline pigment formation under typical growth conditions. These include a temperature between about 20 and about 35° C. for a time between about 2 and about 30 days. As previously mentioned, it is necessary to have good mixing to ensure dispersion of the inducing agent and good aeration of the culture medium to ensure continued fungal growth. However, the addition of the crystalline pigment inducers does not impose any requirements, other than adequate mixing, not previously recognized for precursor pigment production by fermentation of a Monascus species. After an appropriate fermentation period, the crystalline pigment may be harvested by suitable means.

The following examples are merely illustrative of our invention and do not serve to limit its scope in any way.

EXAMPLE I

Isolation of a Monascus Species. Monascus fungi are readily isolated from Chinese fermented food. The particular microorganism used was isolated from a sample of Fukien style red sauce obtained from a local Chinese restaurant. The red paste was streaked out for isolation of individual colonies on a solid cerelose and starch (5%) medium containing 1% proteose peptone, 1.5% agar. Individual fungal colonies producing red pigments were recloned in the same medium and an isolate that produced the most red color as judged by its color intensity, was chosen for all further experiments.

Typical Fermentation of Monascus. The Monascus fungus described above was maintained on agar slants containing (per liter of medium) yeast extract (3 grams), malt extract (3 grams), bacto peptone (5 grams), glucose (10 grams), and agar (15 grams). The slants were inoculated with Monascus fungus and incubated at 30° C. for two weeks. Under these conditions the fungus makes stable sexual spores that can be stored at 4° C. for months.

A slant was used to inoculate a growth medium of approximately 100 mL of broth containing (per liter) glucose (40 g), yeast extract (10 g), $KH_2PO_4$ (3 g), and 0.1–10 mL of TWEEN-40. The TWEEN-40 in the growth medium prevents the cells from inducing pigment synthesis and allows the fungus to grow as a dispersed mycelium. The culture is incubated at 30° C. in a 250 mL flask with shaking at 200 rpm for 1 week.

A 10% inoculum of the above broth culture is used to inoculate 1 to 20 liters of a pigment production medium which contains (per liter of medium) $KH_2PO_4$ (1 g), $MgSO_4 7H_2O$ (0.5 g), NaCl (0.5 g), $FeSO_4 \cdot 7H_2O$ (0.1 g), $NH_4Cl$ (0.5 g), glucose (40 g), and crystalline pigment inducer where appropriate. This culture was incubated at 28° C. with aeration, generally for about 2 weeks. Under these growth conditions the fermentation drops the pH of the medium to approximately 3.0 and pigment production is induced. After the glucose in the fermentation medium is exhausted and maximal pigment has been produced the precursor pigment crystals were harvested.

EXAMPLE II

Crystalline Pigment Production by TWEENS. Monascus fungus isolated from fermented red rice was grown in the fermentation medium, described in Example I, which contained 1 weight percent of various TWEEN's as a crystal inducer. Results are given in Table 1, where "large" crystals are defined as those at least 10 microns long and "small" crystals are those under 10 microns in length.

TABLE 1

Induction of Crystal Formation by Different TWEEN Compounds

| INDUCER | CRYSTAL FORMATION | |
| --- | --- | --- |
|  | 3 DAYS | 17 DAYS |
| TWEEN-20 | few, small | many, large |
| TWEEN-40 | few, large | many, large |
| TWEEN-60 | few, small | few, small |
| TWEEN-80 | none | many, large |

EXAMPLE III

Liquid Vegetable Oils as Crystal Inducers. The aforementioned Monascus species was grown in the production medium described in Example I, which contained liquid vegetable oils at different levels with the results summarized in Table 2. When used at the 10 weight percent level the vegetable oils exhibited good aeration and growth of the fungus in a shake flask culture.

TABLE 2

Induction of Crystal Formation by Different Vegetable Oils

| OIL | CRYSTAL FORMATION | |
| --- | --- | --- |
| (WEIGHT 5) | 9 DAYS | 17 DAYS |
| CORN (1.0%) | few, small | many, small |
| CORN (10.0%) | none | none |
| SOYBEAN (1.0%) | few, small | many, small |
| SOYBEAN (10.0%) | none | none |

EXAMPLE IV

Triglycerides as Crystal Inducers. Monascus species was grown as described in the prior two examples but with the addition of 1 weight percent of various triglycerides to the production medium.

TABLE 3

Induction of Crystal Formation by Different Glycerol Fatty Acid Esters

| TRIGLYCERIDE | CRYSTAL FORMATION | |
| --- | --- | --- |
|  | 4 DAYS | 12 DAYS |
| TRIACETIN | none | few, small |
| TRIARACHIDIN | none | few, small |
| TRIBEHENIN | none | none |
| TRIBUTYRIN | few, small | few, small |
| TRICAPRIN | none | none |
| TRICARDIN | none | none |
| TRICAPRYLIN | none | none |
| TRI-11-EICOSANOIN | none | none |
| TRIELAIDIN | none | none |
| TRIERUCIN | none | none |
| TRILAURIN | none | none |
| TRILINOLEIN | none | none |
| TRILINOLENIN | none | few, small |
| TRIMYRISTIN | none | none |
| TRIOLEIN | few, small | many, large |
| TRIPALMITIN | few, small | few, small |
| TRIPALMITOLEIN | few, small | many, large |
| TRIPETROSELININ | few, small | many, large |
| TRISTEARIN | none | none |
| CONTROL | none | none |

What is claimed is:

1. A process of inducing crystalline precursor pigment formation from Monascus species producing the precursor pigment in a pigment producing culture medium at a level of at least 30 milligrams per liter comprising growing said Monascus species in a pigment producing culture medium containing a crystalline pigment inducer in an amount effective to induce crystalline pigment formation.

2. The process of claim 1 where the Monascus species is selected from the group consisting of M. anka, M. purpureus, M. Major, and M. rubiginosus.

3. The process of claim 1 where the crystalline pigment inducer is a poly(oxyethylene)sorbitan ester of palmitic acid.

4. The process of claim 1 where the crystalline pigment inducer is a liquid vegetable oil.

5. The process of claim 1 where the crystalline pigment inducer is the triglyceride of palmitic, oleic, palmitoleic, petroselinic acids, or any combination of them.

6. The process of claim 1 where the crystalline pigment inducer is a glycerol triester having at least 1 of its acid components selected from the group consisting of palmitic, oleic, palmitoleic, and petroselinic acid.

* * * * *